(12) United States Patent
Nambiar et al.

(10) Patent No.: US 7,511,148 B2
(45) Date of Patent: Mar. 31, 2009

(54) PROCESS FOR PREPARING THIAZOLIDINEDIONES

(75) Inventors: Sudhir Nambiar, Thane (IN); Abhinay Chandrakant Pise, Thane (IN)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/577,121

(22) PCT Filed: Oct. 27, 2004

(86) PCT No.: PCT/EP2004/012149

§ 371 (c)(1),
(2), (4) Date: Feb. 22, 2007

(87) PCT Pub. No.: WO2005/049610

PCT Pub. Date: Jun. 2, 2005

(65) Prior Publication Data

US 2007/0276012 A1    Nov. 29, 2007

(30) Foreign Application Priority Data

Oct. 28, 2003 (GB) ................................ 0325174.1

(51) Int. Cl.
*C07D 417/12* (2006.01)
*C07D 405/12* (2006.01)

(52) U.S. Cl. ................... 546/269.7; 548/183

(58) Field of Classification Search ............. 546/269.7; 548/183
See application file for complete search history.

(56) References Cited

FOREIGN PATENT DOCUMENTS

EP         0816340 A    1/1998
WO    WO 02/051823 A    7/2002

OTHER PUBLICATIONS

Patent Abstracts of Japan, vol. 1999, No. 05; May 31, 1999 & JP 11 049763 A (SANKYO Co Ltd), Feb. 23, 1999 cited in the application abstract paragraph '0061.

Sohda T et al: Studies on antidiabetic agents. Synthesis and hypoglycemic activity of 5-A4-(pyridylallkoxy)benzylU-Arzneimittel Forschung. Drug Research, Edition Cantor. Aulendorf, De, vol. 40, No. 1, Jan. 1990, pp. 37-42.

*Primary Examiner*—Patricia L Morris
(74) *Attorney, Agent, or Firm*—Luedeka, Neely & Graham, P.C.

(57) ABSTRACT

This invention provides a process for reducing an exocyclic double bond at the 5-position of a thiazolidinedione moiety of a thiazolidinedione precursor comprising the steps of:
a) preparing a solution or suspension of the thiazolidinedione precursor in a non-ether solvent medium with a base, and
b) combining the solution or suspension with a dithionite source.

Preferred solvent media include aqueous N,N-dimethylformamide. Sodium dithionite is a preferred dithionite source.

18 Claims, No Drawings

PROCESS FOR PREPARING THIAZOLIDINEDIONES

This application claims benefit under 35 U.S.C. §119(a)-(d) of foreign application GB 0325174., filed on Oct. 28, 2003, which contents are incorporated herein by reference in their entirety.

The present invention relates to a new process for preparing thiazolidinedione compounds which includes the step of reduction of a thiazolidinedione precursor. More particularly, the present invention relates to preparation of thiazolidinedione compounds having antihyperglycemic properties.

Thiazolidinedione antihyperglycemic compounds represent a class of pharmaceuticals which act principally by decreasing insulin resistance in patients suffering from non-insulin-dependent diabetes. Therefore thiazolidinedione antihyperglycemic compounds are used typically as active substances in various pharmaceutical preparations for the treatment of type II diabetes and other disorders related to insulin resistance.

Pioglitazone (5-[[4-[2-(5-ethyl-2-pyridinyl)ethoxy]phenyl]methyl]-2,4-thiazolidinedione, according to Merck Index/13th Edition/Monograph number 7533, CAS Registry number: 111025-46-8) has the formula I

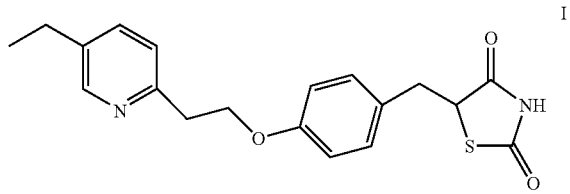

and is used as active substance in pharmaceutical preparations which are used as oral antihyperglycemic agents.

Pioglitazone is currently marketed as pioglitazone hydrochloride (5-[[4-[2-(5-ethyl-2-pyridinyl)ethoxy]phenyl]methyl]-2,4-thiazolidinedione monohydrochloride).

Rosiglitazone (5-[[4-[2-(methyl-2-pyridinylamino)ethoxy]phenyl]methyl]-2,4-thiazolidinedione, according to Merck Index/13th Edition/Monograph number 8346, CAS Registry number: 122320-73-4), and troglitazone (5-[[4-[(3,4-dihydro-6-hydroxy-2,5,7,8-tetramethyl-2H-1-benzopyran-2-yl)methoxy]phenyl]methyl]-2,4-thiazolidinedione, according to Merck Index/13th Edition/Monograph number 9838, CAS Registry number: 97322-87-7) are other thiazolidinedione antihyperglycemic compounds useful for treating type II diabetes and other disorders related to insulin resistance.

Processes for making pioglitazone, rosiglitazone and troglitazone may proceed via a thiazolidinedione precursor having an exocyclic carbon-carbon double bond at the 5-position of the thiazolidinedione moiety. In such methods, the carbon-carbon double bond is e.g. hydrogenated to a carbon-carbon single bond to form the thiazolidinedione antihyperglycemic compound; inter alia, catalytic hydrogenation over a supported catalyst may be applied as known.

A method for making pioglitazone, for example, is disclosed in U.S. Pat. No. 5,952,509. Most known processes comprise demanding methods involving e.g. the above mentioned catalysts, or e.g. the use of cobalt ions. These methods apply agents which are either relatively expensive and/or ecologically critical regarding their handling, and which are often combined with the use of hydrogen under high pressures, the handling of which requires costly safety measures and special reaction apparatus.

Published Japanese patent application 9-213107 discloses use of a dithionite salt with an ether solvent in manufacture of 5-benzylthiazolidin-2,4-dione derivatives.

Surprisingly, the present inventors have found that reduction of the thiazolidinedione precursor to form the corresponding thiazolidinedione antihyperglycemic compound may be effected in a simple and cost-effective way by avoiding ether solvents, which makes it more attractive from an industrial and ecological point of view.

In one aspect therefore, the present invention provides a process for reducing an exocyclic double bond at the 5-position of a thiazolidinedione moiety of a thiazolidinedione precursor comprising the steps of:
a) preparing a solution or suspension of the thiazolidinedione precursor in a non-ether solvent medium with a base, and
b) combining the solution or suspension with a dithionite source.

The dithionite source may comprise sodium-, lithium-, potassium-, calcium-, magnesium-, a tetraalkylammonium- or a guanidinium-dithionite.

Without wishing to be bound by any particular mechanism or theory, the present applicants believe that the dithionite source acts as a reducing agent.

The solution or suspension of the thiazolidinedione precursor in the solvent medium with the base may be combined with the dithionite source at elevated temperatures.

In another aspect, the process of the present invention may further comprise isolation of the reduced thiazolidinedione precursor.

In another aspect, the present invention provides a process for preparing a thiazolidinedione antihyperglycemic compound comprising reduction of the exocyclic double bond at the 5-position of a thiazolidinedione moiety of a thiazolidinedione precursor, especially a thiazolidinedione precursor of pioglitazone, rosiglitazone, or troglitazone, which process comprises the steps of:
a) preparing a solution or suspension of the thiazolidinedione precursor in a non-ether solvent medium with a base, and heating the solution or suspension to a temperature of about 40° C. to 100° C.,
b) combining the solution or suspension with a dithionite source selected from the group of sodium-, lithium-, potassium-, calcium-, magnesium-, a tetraalkylammonium- or a guanidinium-dithionite, to provide a reaction mixture,
c) maintaining the reaction mixture at a temperature of about 40° C. to 100° C. for about 1 to 10 hours, and
d) isolating the resulting thiazolidinedione antihyperglycemic compound as free base.

The reaction mixture may be cooled to about 0° C. to 30° C. before isolation of the thiazolidinedione antihyperglycemic compound.

The applicants understand "non-ether" solvent to mean a solvent which is free of, or substantially free of, any —C—O—C— linkage. Any ether solvent present, i.e. a solvent having a —C—O—C— linkage, is present in trace amounts only, e.g. up to about 5 wt-%, e.g. 0.1 to 3 wt-%, for example 2, 1.5, 1 or 0.5 wt-% or less, based on the total weight of the solvent medium.

The present invention provides therefore a process for preparing pioglitazone including the step of reducing the pioglitazone precursor 5-[4-[2-(5-ethyl-2-pyridinyl)ethoxy]phenyl]methenyl-2,4-thiazolidinedione comprising the above mentioned steps and isolating pioglitazone free base.

In a further aspect, the present invention provides a process for preparing rosiglitazone including the step of reducing the rosiglitazone precursor 5-[4-[2-(methyl-2-pyridinylamino)ethoxy]phenyl]methenyl-2,4-thiazolidinedione comprising the above mentioned steps and isolating rosiglitazone free base.

In still a further aspect, the present invention provides a process for preparing troglitazone including the step of reducing the troglitazone precursor 5-[4-[(3,4dihydro-6-hydroxy-2,5,7,8-tetramethyl-2H-1-benzopyran-2-yl)methoxy]phenyl]methenyl-2,4-thiazolidinedione comprising the above mentioned steps and isolating troglitazone free base.

In another aspect of the invention, the selective reduction process as herein described may take place in the presence of a phase-transfer catalyst.

Depending on the thiazolidinedione precursor selected, the process as described herein may lead to the corresponding thiazolidinedione antihyperglycemic compound in the form of the free base, which is obtained, e.g. in crystalline form, in a high yield and with high purity.

The free base of the thiazolidinedione antihyperglycemic compound may be further purified and/or converted to a derivative, e.g. to a pharmaceutically acceptable salt, e.g. to the hydrochloride in the case of pioglitazone, or e.g. to the maleate in the case of rosiglitazone, by known methods.

A "thiazolidinedione precursor" as used herein, is understood to mean a compound which is an intermediate in a process for making a thiazolidinedione antihyperglycemic compound, such as the process disclosed in U.S. Pat. No. 5,952,509, incorporated herein by reference, and that has a thiazolidinedione moiety.

A preferred thiazolidinedione precursor is a precursor which differs structurally from the corresponding thiazolidinedione antihyperglycemic compound itself in that the preferred thiazolidinedione precursor has an exocyclic double bond at the 5-position of the thiazolidinedione moiety.

A preferred thiazolidinedione precursor may have protected functional groups e.g. protected hydroxyl groups.

The selective reduction of the above mentioned exocyclic double bond, and removal of protecting groups if any, yields the thiazolidinedione antihyperglycemic compound which may subsequently be isolated from the reaction mixture.

The compound 5-[4-[2-(5-ethyl-2-pyridinyl)ethoxy]phenyl]methenyl-2,4-thiazolidinedione, having the formula II

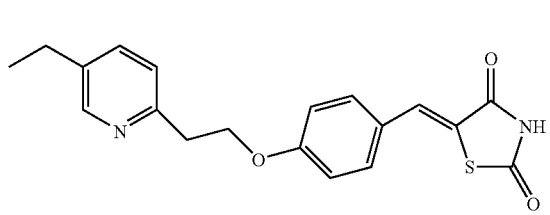

II is an example of a preferred thiazolidinedione precursor for pioglitazone, which may be prepared according to the method of Saito et al. disclosed in U.S. Pat. No. 5,952,509, or in published European patent application EP 0 816 340.

The compound 5-[4-[2-(methyl-2-pyridinylamino)ethoxy]phenyl]methenyl-2,4-thiazolidinedione is an example of a preferred thiazolidinedione precursor for rosiglitazone, and is disclosed, for example, in U.S. Pat. No. 5,002,953.

The compound 5-[4-[(3,4-dihydro-6-hydroxy-2,5,7,8-tetramethyl-2H-1-benzopyran-2-yl) methoxy]phenyl]methenyl-2,4-thiazolidinedione, or hydroxy group protected derivatives thereof, are examples of preferred thiazolidinedione precursors for troglitazone, as disclosed e.g. in J. Crossy et al., Bioorganic and Medicinal Chemistry Letters 9, pp. 3439, 1999.

In one embodiment, the process according to the present invention is carried out as follows:

A solution or suspension is prepared by combining a thiazolidinedione precursor, e.g. a preferred thiazolidinedione precursor of pioglitazone, e.g. 5-[4-[2-(5-ethyl-2-pyridinyl)ethoxy]phenyl]methenyl-2,4-thiazolidinedione, with 5 to 100 volumes of a suitable solvent medium, and with 1 to 30 molar equivalents, preferably 5 to 15 molar equivalents, of a suitable base. Molar equivalents mean "as compared to the thiazolidinedione precursor used".

Suitable bases comprise an alkaline or alkaline earth carbonate, e.g. sodium carbonate, potassium carbonate or lithium carbonate, an alkaline hydrogen carbonate, e.g. sodium bicarbonate, an organic secondary or tertiary amine, e.g. piperidine, or an amidine, e.g. DBU (i.e. 1,8-diazabicyclo [5.4.0]undec-7-en). Preferred bases comprise sodium carbonate or potassium carbonate.

A suitable solvent medium may comprise an aqueous medium, which includes water or a mixture of water with one or more non-ether organic solvents, wherein the ratio of water to organic solvents may be 10:1 to 1:10 (v/v). Thus the solvent medium may comprise a solvent and a co-solvent.

Suitable organic solvents include alcohols, for example methanol, ethanol or isopropanol; alkyl esters such as ethyl acetate; aromatic hydrocarbons, e.g. toluene or xylene; halogenated hydrocarbons, e.g. methylene chloride; amides, e.g. N,N-dimethylformamide or N,N-dimethylacetamide, or a urea, e.g. urea or a tetra-alkylurea such as tetra-methylurea. A preferred solvent medium is N,N-dimethylformamide and water.

The present applicants have found that the use of the DMF/water solvent medium serves to provide that the unsaturated precursor is present typically in amounts below 0.1 wt-% in the final product, reproducibly. This is especially important since the separation of the unsaturated precursor from the reduced product is not possible as a practical matter, economically, through known purification methods. It has been observed that in other solvent mixtures, the poor solubility of the precursor often causes its undesired and unexpected precipitation which makes the reduction non-reproducible.

The ratio of DMF:water may range from 1:1 to 1:10, e.g. 1:2 (v/v) to 1:4 (v/v).

The resulting mixture of the thiazolidinedione precursor, the base and the solvent medium, is subsequently heated to an elevated temperature of about 40° to 100° C., preferably of about 50° C. to 90° C., most preferably of about 60° C. to 80° C.

At the elevated temperatures as mentioned above, 1 to 30 molar equivalents, preferably 5 to 20 molar equivalents (as compared to the thiazolidinedione precursor used), of the dithionite source may be added either in portions or, e.g. drop-wise, as a solution, preferably in water, over a period of a few minutes up to 2 hours, preferably over a period of about 30 min to 1 hour. The resulting reaction mixture is subsequently maintained at the above mentioned elevated temperature during the reduction process, which lasts for about 1 to 10 hours depending on the temperature employed, e.g. for about 1 to 3 hours if the temperature is maintained at about 80° C.

Suitable dithionite sources comprise sodium-, lithium-, potassium-, calcium-, magnesium-, aluminium-dithionite, or a tetraalkylammonium-dithionite, e.g. a tetraethylammonium-dithionite, or a guanidinium-dithionite. A preferred dithionite source is sodium dithionite.

After the completion of the reduction process as herein described, the reduced thiazolidinedione precursor may be isolated from the reaction mixture.

Depending on the solvent or solvent mixture used, the reaction mixture may be cooled to induce or enhance crystallization. The cooling procedure may be effected stepwise, e.g. in a first step to a temperature of about 50° C., and subsequently to about 30° C. to 0° C., preferably to about 10° C. Alternatively, the cooling procedure may be performed so as to provide a substantially constant rate of temperature decrease.

If necessary, and depending on the solvent medium and base used, the pH-value may be adjusted to about 2 to 8, preferably to about 5 to 6, most preferably to about 6, by adding, e.g. acetic acid, e.g. 50 to 60% (v/v) aqueous acetic acid.

The precipitate formed may subsequently be collected by conventional methods such as filtration, washing and vacuum drying.

The resulting free base of the thiazolidinedione antihyperglycemic compound, e.g. pioglitazone free base, may be obtained, e.g. in crystalline form, with good to excellent yields, e.g. of about 55 to 90%, e.g. 70 to 90% (as related to the corresponding thiazolidinedione precursor), and having a high purity, e.g. as defined by a HPLC-purity of about 80% to 98% with respect to impurities and depending on the solvent or solvent mixture used.

If the reduction process takes place in the preferred solvent mixture, i.e. N,N-dimethyl-formamide and water, purity may typically exceed 95%, and the resulting pioglitazone free base may be converted directly to pioglitazone hydrochloride.

In another embodiment, the reduction process as described above may be carried out in the presence of a phase-transfer catalyst. A suitable phase-transfer catalyst may comprise e.g. a tetrabutylammonium halide, a tetraethylammonium halide or a benzyl tributylammonium halide. "Halide" as used herein is understood to mean a bromide, chloride or fluoride of the corresponding compound.

The reduction process as described for the present invention is highly selective, which means that side-products may be formed in small amounts only and which may typically be removed during the subsequent processing of the base of the thiazolidinedione antihyperglycemic compound to a purified form of said base and/or to a derivative thereof, e.g. in the case of pioglitazone, a hydrochloride form.

The free base of the thiazolidinedione antihyperglycemic compound may be further purified by known methods, e.g. by tituration with alcoholic solvents, or by standard crystallization procedures, e.g. using organic solvents, e.g. dioxane or N,N-dimethylformamide, as crystallisation solvents.

In a further aspect of the invention, pioglitazone free base as obtained by the process herein described, may be processed to the hydrochloride or other pharmaceutically acceptable salts by known methods, optionally after a purification step as described above.

In a preferred embodiment, pioglitazone free base as obtained by the reduction process of the invention, is converted to the hydrochloride form by dissolving the crystals of the free base in a solvent, e.g. in an alcohol, e.g. ethanol, e.g. in 1 to 10 volumes, preferably 1 to 6 volumes, of ethanol, and a) by adding hydrochloric acid, e.g. aqueous hydrochloric acid, e.g. 1 to 10 volumes, preferably 1 to 6 volumes, of 2 N HCl, or b) by adding an ethanol containing hydrochloric acid, e.g. ethanolic hydrochloric acid, e.g. 1 to 10 volumes, preferably 1 to 6 volumes, of about 20% (w/v) ethanolic hydrochloric acid, at temperatures of e.g. about 40° C. to 70° C., and by subsequently crystallizing the hydrochloride salt from the resulting solution by gradual cooling in order to obtain pure pioglitazone HCl, e.g. with a HPLC-purity of >98%.

Further purification of the pioglitazone HCl obtained as described above may be performed by known methods, e.g. by recrystallization from a solvent selected from the group of N,N-dimethylformamide, dimethyl acetamide, acetic acid, methanol, ethylene glycol, isopropyl alcohol and t-butyl alcohol.

In addition, pioglitazone HCl may be recrystallized from ethanol as disclosed by Sodha et al., Arzneim.-Forschung/Drug Res. 40 (I), No. 1, 1990, pp. 37.

Pioglitazone HCl obtained by the above described conversion of the pioglitazone free base as obtained by the present invention, corresponds to the known anhydrous crystalline form I.

Form I pioglitazone HCl may be used for the conversion to known crystalline pioglitazone form II employing known methods.

In a further aspect of the invention, rosiglitazone free base as obtained by the process herein described, may be processed to the maleate or other pharmaceutically acceptable salt form by known methods, e.g. as described in U.S. Pat. No. 5,741,803, optionally after a purification step as described above for pioglitazone free base.

In a preferred embodiment, rosiglitazone free base as obtained by the process of the invention, may be converted to the maleate form by a) dissolving the crystals of the free base in a solvent, e.g. in acetone, e.g. in 10 to 14 volumes, preferably 10 to 11 volumes, of acetone, and b) adding maleic acid dissolved in e.g. 10 to 15 volumes acetone, c) heating the reaction mixture thus obtained to around 50-60° C. and by subsequently crystallizing the maleate salt from the resulting solution by gradual cooling in order to obtain pure rosiglitazone maleate e.g. with HPLC-purity of >98%.

In another preferred embodiment, rosiglitazone free base as obtained by the process of the invention, may be converted to the maleate form by a) dissolving or suspending crystals of the free base and maleic acid in a solvent, e.g. ethanol, b) heating the suspension at around boiling temperature, c) optionally treating the mixture with charcoal or diatomaceous earth, d) filtering, e) cooling the solution and crystallizing the maleate, and optionally f) isolation and drying of rosiglitazone maleate.

Further purification of the rosiglitazone maleate obtained as described above may be performed by known methods, e.g. by recrystallization from a solvent selected from the group of N,N-dimethylformamide, dimethyl acetamide, acetic acid, methanol, ethylene glycol, isopropyl alcohol and t-butyl alcohol.

The free base of the thiazolidinedione antihyperglycemic compounds obtained according to the invention, and the derivatives thereof, e.g. pioglitazone HCl or rosiglitazone maleate, may be used in the manufacture of pharmaceutical compositions which are useful for the treatment of patients suffering from diabetes type II or diseases in which insulin resistance is the underlying pathophysiological mechanism.

Further aspects of the invention include the use of pioglitazone free base as obtained using the processes described herein for conversion to the hydrochloride or other pharmaceutically acceptable salt form of pioglitazone;

the use of a thiazolidinedione antihyperglycemic compound as obtained using the processes described herein for the manufacture of a medicament for the administration to a mammal in need thereof;

the use of pioglitazone as free base or as hydrochloride as obtained using the processes described herein for the manufacture of a medicament for the administration to a mammal in need thereof;

the use of rosiglitazone free base as obtained using the processes described herein for conversion to the maleate or other pharmaceutically acceptable salt form of rosiglitazone; and the use of a dithionite source in the presence of a non-ether solvent medium to reduce selectively an exocyclic double bond at the 5-position of a thiazolidinedione moiety of a thiazolidinedione precursor to obtain the corresponding thiazolidinedione compound.

The processes of this invention are carried out at ambient atmospheric pressure.

Following is a description by way of example only of processes according to the invention. All temperatures are given in degree Celsius and are uncorrected.

EXAMPLE 1

Preparation of Pioglitazone Free Base Using Sodium Carbonate as Base and a 1:1 Mixture of Dioxane and Water as Solvent Medium To a solution of 19.5 g sodium carbonate in 75 ml water, 5 g of 5-[4-[2-(5-ethyl-2-pyridinyl)ethoxy]phenyl]methenyl-2,4-thiazolidinedione are added followed by 75 ml dioxane in a round-bottomed flask. The resulting mixture is then heated to about 80° C. under agitation. At about 80° C. a solution of 28 g of sodium dithionite in 150 ml water is added drop-wise within about 60 minutes. The reaction mixture is stirred at about 80° C. for approximately one hour, then cooled to about 50° C. and subsequently stirred at about 50° C. for about one hour before cooling to about 10° C. The pH-value is adjusted to about 6 with 50 ml of 60% (v/v) aqueous acetic acid, and the reaction mixture is then stirred at about 10° C. for about 30 minutes. The precipitate formed is filtered, washed with 100 ml water, and the title compound is collected after drying in a vacuum oven for about 8 hours at approximately 65° C.

Yield (crystalline pioglitazone free base): 4.1 g (82% w/w related to 5-[4-[2-(5-ethyl-2-pyridinyl)ethoxy]phenyl]methenyl-2,4-thiazolidinedione) HPLC-purity: 97.2%.

EXAMPLE 2

Preparation of Pioglitazone Free Base Using Potassium Carbonate as Base and a 1:2 Mixture of Dioxane and Water as Solvent Medium The conditions and procedure are followed as for Example 1, but using 15.6 g potassium carbonate instead of 19.5 g of sodium carbonate, and 150 ml dioxane instead of 75 ml, and 14.7 g of sodium dithionite in 75 ml water instead of 28 g of sodium dithionite in 150 ml water.

Yield (crystalline pioglitazone free base): 4.1 g (82% w/w related to 5-[4[2-(5-ethyl-2-pyridinyl)ethoxy]phenyl]methenyl-2,4-thiazolidinedione) HPLC-purity: 97.2%.

EXAMPLE 3

Preparation of Pioglitazone Free Base Using Potassium Carbonate as Base and a Mixture of Ethyl Acetate and Water as Solvent Medium The conditions and procedure of Example 2 are followed, but using a 1:2 mixture of ethyl acetate and water, i.e. a mixture of 75 ml ethyl acetate and 150 ml water, instead of a mixture of dioxane and water, as solvent medium.

Yield (crystalline pioglitazone free base): 3.5 g (70% w/w related to 5-[4-[2-(5-ethyl-2-pyridinyl)ethoxy]phenyl]methenyl-2,4-thiazolidinedione) HPLC-purity: 90%.

EXAMPLE 4

Preparation of Pioglitazone Free Base Using Potassium Carbonate as Base and a Mixture of N,N-dimethylformamide and Water as Solvent Medium The conditions and procedure of Example 2 are followed, but using a 1:6 mixture of N,N-dimethylformamide and water, i.e. a mixture of 25 ml of N,N-dimethylformamide and 150 ml water, instead of a mixture of dioxane and water, as solvent medium.

Yield (crystalline pioglitazone free base): 3.6 g (72% w/w related to 5-[4-[2-(5-ethyl-2-pyridinyl)ethoxy]phenyl]methenyl-2,4-thiazolidinedione) HPLC-purity: 98%.

EXAMPLE 5

Preparation of Pioglitazone Free Base Using Potassium Carbonate as Base and Water as Solvent Medium The conditions and procedure of Example 2 are followed, but using 225 ml water instead of a mixture of dioxane and water, as solvent medium.

Yield (crystalline pioglitazone free base): 3.7 g (74% w/w related to 5-[4-[2-(5-ethyl-2-pyridinyl)ethoxy]phenyl]methenyl-2,4-thiazolidinedione) HPLC-purity: 89%.

EXAMPLE 6

Preparation of Pioglitazone Free Base Using Sodium Carbonate as Base, a Mixture of Toluene and Water as Solvent Medium and Tetrabutyl Ammonium Bromide as Phase-transfer Catalyst The conditions and procedure are followed as for Example 1, but using a 1:3 mixture of toluene and water, i.e. a mixture of 75 ml toluene and 225 ml water, instead of a mixture of dioxane and water, as solvent medium, and adding 0.5 g tetrabutyl ammonium bromide into the round-bottomed flask before heating the resulting mixture.

Yield (crystalline pioglitazone free base): 4.9 g (98% w/w related to 5-[4-[2-(5-ethyl-2-pyridinyl)ethoxy]phenyl]methenyl-2,4-thiazolidinedione) HPLC-purity: 80%.

EXAMPLE 7

Preparation of Pioglitazone Free Base Using Potassium Carbonate as Base, a Mixture of Ethyl Acetate and Water as Solvent Medium, and Tetrabutylammonium Bromide as Phase-transfer Catalyst The conditions and procedure of Example 6 are followed, but using 15.6 g potassium carbonate instead of sodium carbonate, and a 1:2 mixture of ethyl acetate and water, i.e. a mixture of 75 ml ethyl acetate and 150 ml water, instead of a mixture of toluene and water as solvent medium.

Yield (crystalline pioglitazone free base): 3.5 g (70% w/w related to 5-[4-[2-(5-ethyl-2-pyridinyl)ethoxy]phenyl]methenyl-2,4-thiazolidinedione) HPLC-purity: 90%.

EXAMPLE 8

Preparation of Pioglitazone Hydrochloride from Pioglitazone Free Base Using Ethanolic Hydrochloric Acid 6 g of 5-[[4-[2-(5-ethyl-2-pyridinyl)ethoxy]phenyl]methyl]-2,4-thiazolidinedione, i.e. crystalline free base of pioglitazone as obtained from Example 1, are added to 24 ml ethanol and 12 ml of ethanolic HCl (20% w/v) into a round-bottomed flask. Under stirring the resulting mixture is heated to about 65° C., and is subsequently stirred for about 15 minutes, then gradually cooled to about 30° C. within about 2 hours, again stirred at about 30° C. for one hour, and subsequently further cooled to about 10° C. and stirred for about 1 hour. The precipitate formed is filtered, washed with 30 ml of ethanol, suck-dried, and the title compound is collected after drying under vacuum at about 65° C. for about 10 hours.

Yield (crystalline pioglitazone HCl): 5.7 g (95% w/w related to crystalline pioglitazone free base) HPLC-purity: 99.5%.

EXAMPLE 9

Preparation of Pioglitazone Hydrochloride from Pioglitazone Free Base Using 2 N HCl and Ethanol The conditions and procedure of Example 8 are followed, but using a 1:1 mixture of ethanol and 2 N HCl, i.e. a mixture of 18 ml ethanol and 18 ml 2 N HCl, instead of a mixture of ethanol and ethanolic hydrochloric acid.

Yield (crystalline pioglitazone HCl): 5.4 g (90% w/w related to crystalline pioglitazone free base) HPLC-purity: 99.5%.

EXAMPLE 10

Purification of Pioglitazone Hydrochloride Using Ethanol 6 g crystalline pioglitazone hydrochloride, as obtained from Example 8, are added to 120 ml ethanol in a round-bottomed flask. Under stirring the resulting mixture is heated to about 80° C., and is subsequently stirred for about 30 minutes, then gradually cooled to about 30° C. within about 2 hours, again stirred at about 30° C. for about one hour, and then further cooled to about 10° C. and stirred for approximately 1 hour. The precipitate formed is filtered, washed with 30 ml of ethanol, suck-dried, and the title compound is collected after drying under vacuum at about 65° C. for about 10 hours.

Yield (purified crystalline pioglitazone HCl): 5.4 g (90% w/w related to crystalline pioglitazone hydrochloride) HPLC-purity: 99.9%.

EXAMPLE 11

Preparation of Pure 5-[4-[-(2-pyridinyl)-N-methyl) ethoxy]phenyl]methenyl-2,4-thiazolidinedione (Rosiglitazone Unsaturated Base)

To 100 g 2-chloropyridine, 850 ml N-methyl aminoethanol is added at room temperature and the reaction mixture is heated to about 120° C. under agitation and heated for about 24 hours in round bottom flask. The progress of the reaction is monitored by TLC. After completion of the reaction, the excess of N-methyl aminoethanol is then distilled out under high vacuo at about 80° C. The residue is then cooled to about room temperature and then quenched with water (200 ml) and stirred for about 30 minutes. The aqueous mixture is then extracted with methylene chloride (2*300 ml). The organic layer is then washed with water (2*100 ml), dried over 10 g sodium sulphate and then concentrated under vacuo at about 50° C. to get 127 gm pyridyl ethanol as an oil.

To the suspension of 93.75 g potassium hydroxide in 650 ml dimethyl formamide, 127 g pyridyl ethanol in 325 ml dimethyl formamide are added dropwise at about room temperature within about 60 minutes and the resulting reaction mixture is stirred for about 60 minutes, followed by dropwise addition of 104 g of 4-fluorobenzaldehyde in 325 ml dimethyl formamide in about 60 minutes. The reaction mixture is now stirred at about 40° C. for about 24 hrs. The progress of the reaction is monitored by TLC.

After completion of the reaction, reaction mixture is cooled to about room temperature and then quenched with 2.54 Lt water and stirred for about 30 minutes. It is then extracted with 2*508 ml methylene chloride and then organic layer is washed with 3*1.2 Lt water, dried over 25 g sodium sulphate and then concentrated under vacuo at about 45° C. to get 182 g pyridyl benzaldehyde as an oil.

To the solution of 182 g pyridyl benzaldehyde, 910 ml toluene are added followed by the addition of 83 g 2,4-thiazolidinedione and catalytic amount of piperidinum acetate. The resulting mixture is then refluxed, with removal of water using dean stark apparatus, for about 5 hours. The resulting mixture is then cooled to about room temperature and the separated solid is filtered and suck dried to get 201 g of 5-[4-[N-(2-pyridinyl)-N-methyl) ethoxy]phenyl]methenyl-2,4-thiazolidinedione.

The suck dried material is then purified by stirring at about room temperature using 1000 ml dimethyl formamide for about 1 hour. The suspension is then cooled to about 0-5° C. and stirred at this temperature for about 2-3 hours and then filtered, washed with methanol and then vacuum dried at about 70° C. for approximately 10 hours to get pure 160.8 g of 5-[4-[N-(2-pyridinyl)-N-methyl) ethoxy]phenyl]methenyl-2,4-thiazolidinedione.

EXAMPLE 12

Preparation of Pure 5-[4-[N-(2-pyridinyl)-N-methyl) ethoxy]phenyl]methyl-2,4-thiazolidinedione (Rosiglitazone Base)

To a solution of 14 g potassium carbonate in 25 ml water, 5 g of 5-[4-[N-(2-pyridinyl)-N-methyl)ethoxy]phenyl]methenyl-2,4-thiazolidinedione are added followed by 25 ml dimethyl formamide in a round bottom flask. The resulting solution is then heated to about 80° C. under agitation. At about 80° C. a solution of 9 g of sodium dithionite in 90 ml water is added drop wise within about 60 minutes. The reaction mixture is stirred at about 80° C. for approximately two hours and then cooled to about 50° C. It is subsequently stirred at about 50° C. for about two hours before cooling to about 10° C. and the reaction mixture is then stirred for about two hours. The precipitate is filtered, washed with 100 ml water, and the title compound is collected after drying in a vacuum oven for about 8 hours at approximately 65° C.

Yield (crystalline rosiglitazone free base): 3.0 g (60% w/w related to 5-[4-[N-(2-pyridinyl)-N-methyl) ethoxy]phenyl] methenyl-2,4-thiazolidinedione) HPLC -Assay: 99 %.

EXAMPLE 13

Preparation of 5-[4-[N-2-pyridinyl)-N-methyl) ethoxy]phenyl]methyl-2,4-thiazolidinedione maleate from 5-[4-[N-2-pyridinyl)-N-methyl)ethoxy]phenyl] methyl-2,4-thiazolidinedione A mixture of 4.0 g 5-[[4-[2-(methyl-2-pyridinylamino) ethoxy]phenyl]methyl]-2,4-thiazolidinedione and 1.31 g maleic acid are stirred in 37 ml absolute ethanol and heated at boiling temperature until a clear solution is obtained. 0.4 g charcoal is added and after 5 min the hot solution is filtered and allowed to cool to room temperature under stirring. After standing in a refrigerator at 4° C. for 17 hours, the precipitated product is filtered and dried at 50° C. under vacuum for 20 hours to give 3.9 g (73%) of the product.

The following Table A indicates HPLC analyses for rosiglitazone (ROS-90) and the precursor 5-[4-[N-(2-pyridinyl)-N-methyl)ethoxy]phenyl]methenyl-2,4-thiazolidinedione abbreviated "ROS-60". The amounts of unreacted precursor are very low for ethanol/water, methanol/water and DMF/water solvent media. The reaction conditions used are as used above, or analogous to the above reaction parameters. The HPLC results are area-%.

TABLE A

| No. | Solvent Ratio per g ROS-60 | | | Solvent medium | | HPLC analysis Area % | |
|---|---|---|---|---|---|---|---|
| | ROS-60 | Co-solvent | Water (ml) | Co-solvent | Solvent | ROS-90 | ROS-60 |
| A1 | 5 g | 25 ml | 115 | Water | Water | 95.09 | 3.5 |
| A2 | 5 g | 25 | 115 | THF | Water | 96.53 | 2.59 |
| A3 | 5 g | 25 | 115 | Ethanol | Water | 97.21 | 0.1 |
| A4 | 5 g | 25 | 115 | Methanol | Water | 91.9 | 0.13 |
| A5 | 5 g | 25 | 115 | Dioxane | Water | 93.35 | 1.08 |
| A6 | 5 g | 25 | 115 | DMF | Water | 99.1 | 0.05 |

Experiments: Pioglitazone

REFERENCE EXAMPLE 1

Preparation of 5-[4-[2-(5-ethyl-2-pyridinyl)ethoxy] phenyl]methenyl-2,4-thiazolidinedione from 5-Ethyl-2-pyridine Ethanol 10 g of 5-ethyl-2-pyridine ethanol, 10.2 ml triethylamine and 75 ml toluene are added to the round bottom assembly at ambient temperature. Thereafter 6.16 ml methane sulfonyl chloride are added via dropping funnel in 1 hour. The reaction mixture is stirred at ambient temperature for 1 hour and then washed with water. To the toluene layer are added 22.6 ml PEG200, 13.6 g potassium carbonate and 12 g 4-hydroxy benzaldehyde and the reaction mixture stirred for 4 hours at 80° C. The reaction mixture is cooled to ambient temperature and washed with 1 N alkali followed by water. Toluene is distilled off to obtain 4[2-(5-ethyl-2-pyridyl)ethoxy]benzaldehyde as oil to which are added methanol, pyrrolidine followed by 2,4-thiazolidinedione. The reaction mixture is stirred at 50° C. for 6 hours and then cooled to 10° C. Stirring is continued at 10° C. for 2 hours and the mixture filtered to obtain 5-[4[2-(5-ethyl-2-pyridinyl)ethoxy]phenyl]methenyl-2,4-thiazolidinedione. The wet cake is washed with Methanol.

Yield: 11 g (110% w/w related to 5-Ethyl-2-pyridine ethanol) HPLC-purity: 98 %.

REFERENCE EXAMPLE 2

Preparation of Pioglitazone Free Base Using Potassium Carbonate as Base and a Mixture of N,N-dimethylformamide and Water as Solvent Medium To a solution of 23.4 g potassium carbonate in 270 ml water, 10 g of 5-[4-[2-(5-ethyl-2-pyridinyl)ethoxy]phenyl] methenyl-2,4-thiazolidinedione are added in a round-bottomed flask. The resulting mixture is then heated to about 80° C. under agitation. At about 80° C. a solution of 29.5 g of Sodium dithionite in 150 ml water is added drop-wise within about 60 minutes. Then added 150 ml of N,N-dimethylformamide and the reaction mixture is stirred at about 80° C. for approximately 3 hours and then cooled to about 10° C. and the reaction mixture is then stirred at about 10° C. for about 30 minutes. The precipitate is filtered, washed with 100 ml water, and the title compound is collected after drying in a vacuum oven for about 8 hours at approximately 65° C.

Yield: 5.5 g (55% w/w related to 5-[4-[2-(5-ethyl-2-pyridinyl)ethoxy]phenyl]methenyl-2,4-thiazolidinedione) HPLC-purity: 99% (PG60<0.05%)

REFERENCE EXAMPLE 3

Preparation of Pioglitazone Free Base Using Potassium Carbonate as Base and a Mixture of Ethanol and Water as Solvent Medium To a solution of 23.4 g potassium carbonate in 150 ml water, 10 g of 5-[4-[2-(5-ethyl-2-pyridinyl)ethoxy]phenyl] methenyl-2,4-thiazolidinedione are added in a round-bottomed flask. The resulting mixture is then heated to about 80° C. under agitation. At about 80° C. a solution of 29.5 g sodium dithionite in 100 ml water is added drop-wise within about 60 minutes. 50 ml ethanol are added and the reaction mixture stirred at about 80° C. for approximately 3 hours, cooled to about 10° C. and the reaction mixture stirred at about 10° C. for about 30 minutes. The precipitate is filtered, washed with 100 ml water, and the title compound is collected after drying in a vacuum oven for about 8 hours at approximately 65° C.

Yield: 5.5 g (55% w/w related to 5-[4-[2-(5-ethyl-2-pyridinyl)ethoxy]phenyl]methenyl-2,4-thiazolidinedione)

HPLC-purity: 97% (PG60~0.3%)

REFERENCE EXAMPLE 4

Preparation of Pioglitazone Free Base Using Potassium Carbonate as Base and a Mixture of Methanol and Water as Solvent Medium To a solution of 23.4 g potassium carbonate in 150 ml water, 10 g of 5-[4-[2-(5-ethyl-2-pyridinyl)ethoxy]phenyl]methenyl-2,4-thiazolidinedione are added in a round-bottomed flask. The resulting mixture is then heated to about 80° C. under agitation. At about 80° C. a solution of 29.5 g sodium dithionite in 100 ml water is added drop-wise within about 60 minutes. 50 ml methanol are added and the reaction mixture is stirred at about 65° C. for approximately 3 hours, cooled to about 10° C., and stirred at about 10° C. for about 30 minutes. The precipitate is filtered, washed with 100 ml water, and the title compound collected after drying in a vacuum oven for about 8 hours at approximately 65° C.

Yield: 5.2 g (52% w/w related to 5-[4-[2-(5-ethyl-2-pyridinyl)ethoxy]phenyl]methenyl-2,4-thiazolidinedione)

HPLC-purity: 95% (PG60~0.5%)

REFERENCE EXAMPLE 5

Preparation of Pioglitazone Free Base Using Potassium Carbonate as Base and a Mixture of Tetrahydrofuran and Water as Solvent Medium To a solution of 23.4 g potassium carbonate in 270 ml water, 10 g of 5-[4-[2-(5-ethyl-2-pyridinyl)ethoxy]phenyl]methenyl-2,4-thiazolidinedione are added in a round-bottomed flask. The resulting mixture is then heated to about 80° C. under agitation. At about 80° C. a solution of 29.5 g sodium dithionite in 150 ml water is added drop-wise within about 60 minutes. 150 ml tetrahydrofuran are added, the reaction mixture stirred at about 65° C. for approximately 3 hours, cooled to about 10° C. and stirred at about 10° C. for about 30 minutes. The precipitate is filtered, washed with 100 ml water, and the title compound is collected after drying in a vacuum oven for about 8 hours at approximately 65° C.

Yield: 4.4 g (44% w/w related to 5-[4-[2-(5-ethyl-2-pyridinyl)ethoxy]phenyl]methenyl-2,4-thiazolidinedione)

HPLC-purity: 99% (PG60~0.5%)

REFERENCE EXAMPLE 6

Preparation of Pioglitazone Free Base Using Potassium Carbonate as Base and a Mixture of 1.4 Dioxane and Water as Solvent Medium To a solution of 23.4 g potassium carbonate in 200 ml water, 10 g of 5-[4-[2-(5-ethyl-2-pyridinyl)ethoxy]phenyl]methenyl-2,4-thiazolidinedione are added in a round-bottomed flask. The resulting mixture is then heated to about 80° C. under agitation. At about 80° C. a solution of 29.5 g sodium dithionite in 100 ml water is added drop-wise within about 60 minutes. 150 ml 1,4 dioxane are added, the reaction mixture stirred at about 80° C. for approximately 3 hours, cooled to about 10° C. and then stirred at about 10° C. for about 30 minutes. The precipitate is filtered, washed with 100 ml water, and the title compound is collected after drying in a vacuum oven for about 8 hours at approximately 65° C.

Yield: 5.0 g (50% w/w related to 5-[4-[2-(5-ethyl-2-pyridinyl)ethoxy]phenyl]methenyl-2,4-thiazolidinedione)

HPLC-purity: 96% (PG60~1%)

The following Table B indicates HPLC analyses for pioglitazone (PG-90) and the precursor 5-[4-[2-(5-ethyl-2-pyridinyl)ethoxy]phenyl]methenyl-2-4,thiazolidinedione abbreviated "PG-60". The amounts of unreacted precursor are very low for DMF/water solvent media in comparison with an ether/water solvent medium. The reaction conditions used are as used above, or analogous to the above reaction parameters. The HPLC results are area-%.

TABLE B

Comparative results for co-solvents used for reduction using sodium dithionite with water as solvent

| | PG-60 | SOLVENT | | COSOLVENT | | HPLC | |
|---|---|---|---|---|---|---|---|
| | | | | | | PG60 | PG90 |
| | (gms) | ml | | | ml | Area % | Area % |
| B1 | 70 | Water | 2940 | DMF | 1050 | 0.04 | 98.77 |
| B2 | 60 | Water | 2520 | DMF | 900 | 0.03 | 97.49 |
| B3 | 70 | Water | 2940 | DMF | 1050 | 0.03 | 98.4 |
| B4 | 70 | Water | 2940 | DMF | 1050 | 0.03 | 97.71 |
| B5 | 30 | Water | 1260 | DMF | 450 | 0.05 | 97.67 |
| B6 | 70 | Water | 2940 | DMF | 1050 | 0.04 | 98.54 |
| B7 | 5 | Water | 125 | Methanol | 25 | 0.50 | 94.51 |
| B8 | 5 | Water | 125 | Methanol | 25 | 0.58 | 90.45 |
| B9 | 5 | Water | 130 | Ethanol | 25 | 0.30 | 97.63 |
| B10 | 5 | Water | 125 | Ethanol | 25 | 0.28 | 96.99 |
| B11 | 6 | Water | 252 | THF | 90 | 0.38 | 99.11 |
| B12 | 6 | Water | 180 | 1,4-Dioxane | 90 | 1.09 | 96.42 |

The preparation of thiazolidinedione antihyperglycemic compounds, e.g. pioglitazone, rosiglitazone, or troglitazone, e.g. in the form of their free bases, by reducing selectively their respective preferred thiazolidinedione precursors by using a dithionite source in the absence of an ether as described in the present invention, involves a novel reduction process which is attractive both from economic and ecological standpoints.

The reduction process of the invention displays the same or similar selectivity related to the reduction of the thiazolidinedione precursors, and leads to the same or similar high yields and high purity of the thiazolidinedione antihyperglycemic compounds, e.g. of the pioglitazone free base and HCl, as hitherto known processes. The process of the present invention offers, however, the advantages of using reaction agents which are readily commercially available, cheap, ecologically "unrisky" and which avoid potentially dangerous handling.

The reaction of this invention using sodium dithionite with an aqueous DMF solvent medium is particularly attractive. Conversion of precursor is substantially more complete than with hitherto known processes.

The invention claimed is:

1. A process for reducing an exocyclic double bond at the 5-position of a thiazolidinedione moiety of a thiazolidinedione precursor comprising the steps of:
   a) preparing a solution or suspension of a thiazolidinedione precursor selected from the group consisting of pioglitazone precursors, rosiglitazone precursors, and troglitazone precursors, in a non-ether solvent medium with a base, and b) combining the solution or suspension with a dithionite source.

2. The process as claimed in claim 1, wherein the solvent medium is water or a mixture of water with one or more organic solvents.

3. The process as claimed in claim 2, wherein the organic solvent is an alcohol, an alkyl ester, an aromatic hydrocarbon, a halogenated hydrocarbon, an amide, a urea, or a mixture thereof.

4. The process as claimed in claim 2, wherein the organic solvent is methanol, ethanol, isopropanol, ethyl acetate, toluene, xylene, methylene chloride, N,N-dimethyl-formamide, or a mixture thereof.

5. The process as claimed in claim 1, wherein the dithionite source is sodium-, lithium-, potassium-, calcium-, magnesium-, a tetraalkylammonium- or a guanidinium-dithionite.

6. The process as claimed in claim 1, wherein the dithionite source is sodium dithionite.

7. The process as claimed in claim 1, wherein the base is an alkaline or alkaline earth carbonate, an alkaline hydrogen carbonate, an organic secondary or tertiary amine or an amidine.

8. The process as claimed in claim 1, wherein the base is sodium carbonate or potassium carbonate.

9. The process as claimed in claim 1, which process takes place in the presence of a phase-transfer catalyst.

10. The process as claimed in claim 1, wherein the phase-transfer catalyst is a tetrabutylammonium halide, a tetraethylammonium halide or a benzyl tributylammonium halide.

11. The process as claimed in claim 1, wherein the thiazolidinedione precursor is 5-[4-[2-(5-ethyl-2-pyridinyl)ethoxy]phenyl]methenyl-2,4-thiazolidinedione or 5-[4-[2-(methyl-2-pyridinylamino)ethoxy]phenyl]methenyl-2,4-thiazolidinedione.

12. The process as claimed in claim 1, wherein the thiazolidinedione precursor is 5-[4-[(3,4-dihydro-6-hydroxy-2,5,7,8-tetramethyl-2H-1-benzopyran-2-yl)methoxy]phenyl]methenyl-2,4-thiazolidinedione.

13. The process as claimed in claim 1, wherein the solution or suspension of the thiazolidinedione precursor in the solvent medium with the base is combined with the dithionite source at a temperature at about 40° C. to 100° C.

14. The process as claimed in claim 1, further comprising the step of isolating the reduced thiazolidinedione precursor.

15. A process for preparing a thiazolidinedione antihyperglycemic compound selected from the group consisting of pioglitazone, rosiglitazone, and troglitazone, comprising reducing the exocyclic double bond at the 5-position of a thiazolidinedione moiety of a corresponding thiazolidinedione precursor which process comprises the steps of:
 a) preparing a solution or suspension of the thiazolidinedione precursor in a non-ether solvent medium with a base, and heating the solution or suspension to a temperature of about 40° C. to 100° C.,
 b) combining the solution or suspension with a dithionite source selected from the group of sodium-, lithium-, potassium-, calcium-, magnesium-, a tetraalkyl- ammonium- or a guanidinium-dithionite, to provide a reaction mixture,
 c) maintaining the reaction mixture at a temperature of about 40° C. to 100° C., and
 d) isolating the resulting thiazolidinedione antihyperglycemic compound as free base.

16. A process for preparing pioglitazone, which process comprises the following steps:
 a) preparing a solution or suspension of 5-[4-[2-(5-ethyl-2-pyridinyl)ethoxy]phenyl]methenyl-2,4-thiazolidinedione in a non-ether solvent medium with a base, and heating the solution or suspension to a temperature of about 60° C. to 80° C.,
 b) combining the solution or suspension with sodium dithionite to provide a reaction mixture,
 c) maintaining the reaction mixture at a temperature of about 60° C. to 80° C., and
 d) isolating pioglitazone as free base.

17. A process for preparing rosiglitazone, which process comprises the following steps:
 a) preparing a solution or suspension of 5-[4-[N-(2-pyridinyl)-N-methyl)ethoxy]phenyl]methenyl-2,4-thiazolidinedione in a non-ether solvent medium with a base, and heating the solution or suspension to a temperature of about 60° C. to 80° C.,
 b) combining the solution or suspension with sodium dithionite to provide a reaction mixture,
 c) maintaining the reaction mixture at a temperature of about 60° C. to 80° C., and
 d) isolating rosiglitazone as free base.

18. The process as claimed in claim 15, wherein the reaction mixture is cooled to about 0° C. to 30° C. before isolation of the thiazolidinedione antihyperglycemic compound.

* * * * *